United States Patent [19]
Blomquist et al.

[11] Patent Number: 5,658,250
[45] Date of Patent: Aug. 19, 1997

[54] SYSTEMS AND METHODS FOR OPERATING AMBULATORY MEDICAL DEVICES SUCH AS DRUG DELIVERY DEVICES

[75] Inventors: Michael L. Blomquist, Coon Rapids; Thomas L. Peterson, Shoreview, both of Minn.

[73] Assignee: SIMS Deltec, Inc., St. Paul, Minn.

[21] Appl. No.: 555,304

[22] Filed: Nov. 8, 1995

Related U.S. Application Data

[63] Continuation of Ser. No. 90,738, Jul. 13, 1993, abandoned.
[51] Int. Cl.$^6$ ................................................ A61M 31/00
[52] U.S. Cl. ..................... 604/65; 604/31; 128/DIG. 12; 128/DIG. 13
[58] Field of Search ..................... 365/900, 185.33; 604/65–67, 151–155; 128/DIG. 12, DIG. 13

[56] References Cited

U.S. PATENT DOCUMENTS

| | | |
|---|---|---|
| 3,809,871 | 5/1974 | Howard et al. . |
| 4,308,866 | 1/1982 | Jelliffe et al. . |
| 4,320,757 | 3/1982 | Whitney et al. . |
| 4,490,798 | 12/1984 | Franks et al. . |
| 4,529,401 | 7/1985 | Leslie et al. . |
| 4,559,038 | 12/1985 | Berg et al. . |
| 4,561,443 | 12/1985 | Hogrefe .................................. 604/65 |
| 4,565,542 | 1/1986 | Berg . |
| 4,578,573 | 3/1986 | Flies et al. . |
| 4,624,661 | 11/1986 | Arimond . |
| 4,650,469 | 3/1987 | Berg et al. . |
| 4,658,371 | 4/1987 | Walsh et al. . |
| 4,676,776 | 6/1987 | Howson . |
| 4,681,563 | 7/1987 | Deckert et al. . |
| 4,722,734 | 2/1988 | Kolln . |
| 4,731,058 | 3/1988 | Doan . |
| 4,741,732 | 5/1988 | Crankshaw et al. . |
| 4,754,401 | 6/1988 | Kaczynski et al. . |
| 4,832,033 | 5/1989 | Maher et al. . |

(List continued on next page.)

FOREIGN PATENT DOCUMENTS

| | | |
|---|---|---|
| 2060151 | 8/1992 | Canada . |
| 0188288 | 7/1986 | European Pat. Off. . |
| 0497041A1 | 8/1992 | European Pat. Off. . |
| 503670 | 9/1992 | European Pat. Off. . |
| 665955A5 | 6/1988 | France . |
| 92/15349 | 9/1992 | WIPO . |
| 94/08647 | 4/1994 | WIPO . |

OTHER PUBLICATIONS

"Microprocessors and Microsystems" vol 14 No 8 Oct. 1990 Saul Zales and Dale Ebert pps. 543–549.
"Byte" Nov. 1990, pps 311–318 Walter Lahti and Dean McCarron.
"Integrated Circuits" of *Computer Design*, Jun. 1, 1989, pps 26–27 Ron Wilson.
Intel® document entitled, "28F001BX-T/28F001BX-B 1M(128Kx8) CMOS Flash Memory", dated Mar., 1991, 28 pages. (Exhibit A).
Intel® document entitled, "28F008SA 8 MB1T (1 MB1Tx8) Flashtile™ Memory", dated Mar., 1992, 28 pages. (Exhbit B).

*Primary Examiner*—Mark Bockelman
*Attorney, Agent, or Firm*—Merchant, Gould Smith, Edell Welter & Schmidt, P. A.

[57] ABSTRACT

The present invention relates to systems and methods for operating ambulatory medical devices, such as drug delivery devices. The pump includes the pump control system for activating a pumping mechanism wherein the pump control system includes a processor, a flash memory electrically interconnected to the processor for storing pump operation information, and a communications port electrically interconnected to the flash memory to permit transfer of the pump information into the flash memory from outside the pump. Communication with the pump can be through a computer system located locally or remotely with respect to the pump. The flash memory is utilized to initially program the pump electronically, or to reprogram the pump to change operation of the pump.

18 Claims, 4 Drawing Sheets

U.S. PATENT DOCUMENTS

| | | |
|---|---|---|
| 4,889,132 | 12/1989 | Hutchenson et al. . |
| 4,908,017 | 3/1990 | Howson et al. . |
| 4,943,279 | 7/1990 | Samiotes et al. . |
| 5,034,004 | 7/1991 | Crankshaw .............................. 604/154 |
| 5,053,990 | 10/1991 | Kreifels ..................................... 365/900 |
| 5,078,683 | 1/1992 | Sancoff et al. . |
| 5,100,380 | 3/1992 | Epstein et al. . |
| 5,131,816 | 7/1992 | Brown et al. . |
| 5,176,004 | 1/1993 | Gaudet . |
| 5,181,910 | 1/1993 | Scanlon . |
| 5,238,001 | 8/1993 | Gallant et al. . |
| 5,256,157 | 10/1993 | Samiotes et al. . |
| 5,265,431 | 11/1993 | Gaudet et al. . |
| 5,317,506 | 5/1994 | Coutré et al. ............................... 604/65 |
| 5,376,070 | 12/1994 | Purvis et al. ............................... 604/65 |

SYSTEMS AND METHODS FOR OPERATING AMBULATORY MEDICAL DEVICES SUCH AS DRUG DELIVERY DEVICES

This is a continuation of application Ser. No. 08/090,738, filed Jul. 13, 1993, now abandoned.

FIELD OF THE INVENTION

The present invention relates generally to ambulatory medical devices and methods for operating such devices. In particular, the present invention relates to drug delivery operating systems and methods for operating drug delivery devices.

BACKGROUND OF THE INVENTION

Various ambulatory medical devices are known for treating and/or monitoring patients at a remote site away from the caregiver's office. One example of an ambulatory medical device is a drug delivery device, such as a drug pump, for providing drug delivery to the patient when the patient is away from the caregiver's office.

Certain drugs rarely achieve their maximum therapeutic action through conventional injection techniques. Many drugs reach their full potential only through precise delivery over an extended period of time. With controlled drug infusion through a drug pump, the drug can be given at a precise rate that will keep the drug concentration within the therapeutic margin and out of the toxic range. Ambulatory drug pumps can provide appropriate drug delivery to the patient at a controllable rate which does not require frequent medical attention and which allows the patient to leave the hospital or caregiver's office.

Existing drug pumps are known to include a processor and a memory device for controlling operation of the pump. In addition, some pumps have various sensors, switches, and devices associated with the pumping operation of the pump.

There is a need for increased sophistication with respect to the drug therapies administered by the drug pumps in order to better treat patients and to reduce health care expenditures by reducing doctor visits and hospital stays.

Controlling operation of the drug pumps in sophisticated therapies is becoming an increasing concern. There is a need for some pumps to be used over a period of time for very different therapies, such as chemotherapy, pain control, nutrition, or antibiotic therapy, for the same or different patients. If the therapy type cannot be changed, or if the therapy type cannot be changed easily, the caregiver must maintain an inventory of pumps with each desired therapy type. Moreover, updates or changes in features of the therapies become a problem if the operating systems of the pumps cannot be changed or if the pumps are not easily changeable. Customization of the pumps is difficult or impossible.

Within each of the broad classes of therapies and other therapies, there are often patient specific parameters which need to be addressed. For example, some desired patient specific parameters may take into account such items as patient weight, and/or the severity of the patient's particular condition. One concern relates to whether and to what extent the pumps can be set for patient specific therapies.

If the pump therapy types and/or the patient specific parameters are changeable, there is a need for these changes to be easy for the caregiver to make. Further, if a problem in the pump operating system develops or if a change in the pump operating system needs to be made when the pump is away from the caregiver's office, this is a further concern.

Also, drug pumps must generally be reliable and durable in the settings in which they are used. Since the pumps are ambulatory, the patient may expose the pump to various environmental conditions and/or impurities that could damage fragile components of the pump. Failure of the drug pump to deliver the appropriate dosage of drug to the patient can be harmful to the patient.

There is a need for operating systems and methods for operating ambulatory medical devices, such as drug pumps, which address at least some of the needs and concerns noted above and other needs and concerns associated with the increasingly sophisticated and complex therapies and devices desired by the health care industry.

SUMMARY OF THE INVENTION

The present invention relates to operating systems and methods for operating an ambulatory medical device, such as a drug delivery device, and in particular, a drug pump. In one aspect of the present invention, a pump is provided including a pump mechanism for pumping fluid from a reservoir through a conduit to the patient. A pump control system is provided for activating the pump mechanism wherein the pump control system includes: a processor for operating the pump mechanism; a flash memory electrically interconnected to the processor for storing at least a portion of pump operation information; and a communications port electrically interconnected to the processor to permit transfer of the pump operation information to the flash memory from an exterior of the pump.

The flash memory permits initial programming and subsequent reprogramming of the pump for any of a variety of different pump operation information to control operation of the pump mechanism and other features of the pump.

The programming of the flash memory takes place through the communications port. Access to the interior of the pump is thereby limited and the interior of the pump is protected from the environment. Further, the communications port is connectable to a computer system located locally to the pump. Alternatively, the pump is connectable through the communications port to a computer system located remotely to the pump, such as via a modem connection arrangement over the telephone lines.

According to another aspect of the invention, a method for pumping fluid to a patient is provided wherein a pump is provided including pumping structure for pumping a fluid to a patient, and pump control structure for activating the pump structure. The pump control structure includes a processor, a flash memory, and a communications port. Pump operation information is electrically input to the flash memory through the communications port and the processor from a source located either locally or remotely to the pump. The pumping structure is operated with the first pump operation information to pump fluid to the patient.

A further aspect of the invention relates to the method above further comprising electrically inputting second pump operation information to the flash memory through the communications port and the processor and then operating the pumping structure with the second pump operation information to pump fluid to the patient. This aspect of the invention can be utilized when the drug therapy program in the flash memory is to be changed. The second pump operation information can be electrically input to the flash memory from a computer system at a location either locally or remotely to the pump.

Other aspects of the invention relate to downloading a diagnostic program to the flash memory before the flash memory is initially programmed or subsequently reprogrammed with a new operations program. Another aspect of the invention relates to utilizing a status program to track the reprogramming of the flash memory and other pump information to generate status information for a status report on the inventory of pumps programmed by the programming source.

BRIEF DESCRIPTION OF THE DRAWINGS

In the drawings, where like numerals refer to like features throughout the several views.

DETAILED DESCRIPTION OF THE PREFERRED EMBODIMENT

Figure 1:
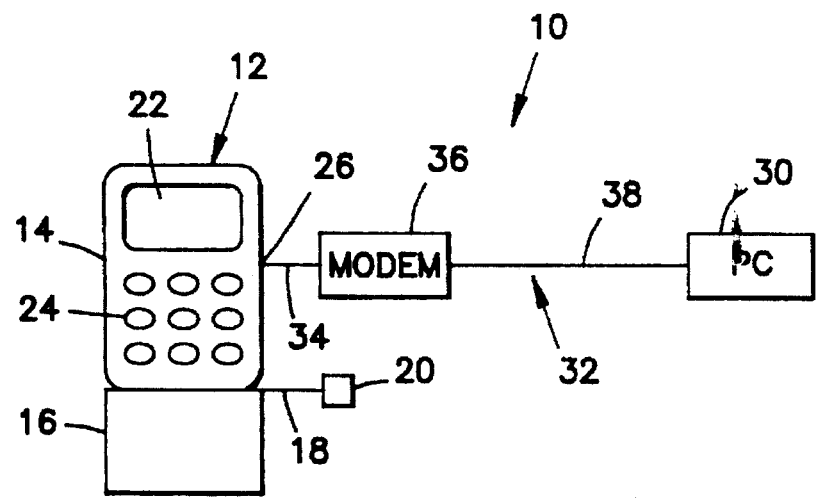
FIG. 1 is a schematic diagram of a drug pump according to the present invention shown linked to a personal computer for communication with the personal computer.

Referring now to FIG. 1, a system 10 for operation of pump 12 is shown. Pump 12 includes a control module 14 and a replaceable cassette 16 mounted thereto. Cassette 16 provides a fluid reservoir for holding the drug or other fluid to be pumped to the patient. Cassette 16 may include the fluid reservoir in an interior of cassette 16. Alternatively, cassette 16 may include a conduit linking cassette 16 to a remote container of fluid (not shown).

Control module 14 includes an outer housing and a pumping mechanism for pumping fluid from the fluid reservoir of cassette 16 through a tube or conduit 18 to a patient. An example of a pumping mechanism is shown in U.S. Pat. No. 4,559,038, incorporated herein by reference. In U.S. Pat. No. 4,559,038, the pumping mechanism includes a rotatable cam shaft which engages a reciprocating inlet valve, a reciprocating expulser, and a reciprocating outlet valve. The valves and expulser engage a flexible tube member associated with cassette 16 where the flexible tube member is interconnected to the fluid reservoir. The rotating camshaft moves the valves and expulser to pump fluid through the tube member to the patient. Other pumping mechanisms are anticipated for pumping fluid to the patient.

Tube 18 extends from pump 12 and terminates at a patient end or port 20. Fluid flows from the fluid reservoir of cassette 16, past the pumping mechanism of control module 14, and through tube 18. Patient port 20 can be interconnected to a patient intravenously.

Control module 14 of pump 12 includes pump control means for activating the pumping mechanism. The pump control means also preferably: controls a display 22; receives inputs from a keyboard 24; and electronically transmits and receives information through an input/output communications port 26. Keyboard 24 includes at least one key. Keyboard 24 in FIG. 1 is shown to include a plurality of individual keys. The pump control means also preferably controls one or more switches, sensors, or devices associated with operation of pump 12.

As will be discussed in more detail below, the pump control means includes a processor 140 for operating the pump mechanism, and a flash memory 150 electrically interconnected to the processor 140 for storing pump operation information (See FIGS. 4A and 4B). The flash memory 150 is electrically interconnected to the communications port 26 to permit transfer of pump operation information to the flash memory 150 from external of the pump.

Communications port 26 permits the downloading of pump operation information from a computer system 30, such as a personal computer. The computer system 30 typically includes a processor, memory, an operator input means such as a keyboard for inputting data, a data input means such as disk, tape, or card reader, and a display means such as a monitor for displaying appropriate information to the operator of computer system 30. Computer system 30 can also be utilized to view the pump operation information including any patient specific settings previously input to the memory in pump 12 to speed the reprogramming of pump 12.

Communication means 32 links computer system 30 and pump 12. Included in communication means 32 is a cable 34 or other communication structure interconnecting communications port 26 of pump 12 to a device 36. Cable 38 or other communications structure interconnects device 36 to computer system 30. Pump 12 is preferably not linked directly to computer system 30, since pump 12 may be provided with one or more power supplies other than conventional 110 volt power supplies used to power computer system 30. Device 36 performs an isolation function in FIG. 1. It is desirable to electrically protect pump 12 from computer system 30 to protect pump 12 and the patient from any hazards, such as electrical shock, associated with the electrical source power for computer system 30. In FIG. 1, device 36 may communicate with computer system 30 through an RS232 serial cable. Similarly, device 36 may communicate with pump 12 through an RS232 serial cable. Device 36 is to be appreciated as an optional device if it is not desired to electrically isolate pump 12 from computer system 30. In that case, an RS232 serial cable can connect pump 12 and computer system 30 directly. As will be discussed below, device 36 is also configured as a modem for use in transmitting data to and receiving data from a remote location, in addition to the structure for local communication with computer system 30 in an isolation function, as shown in FIG. 1.

Figure 3:
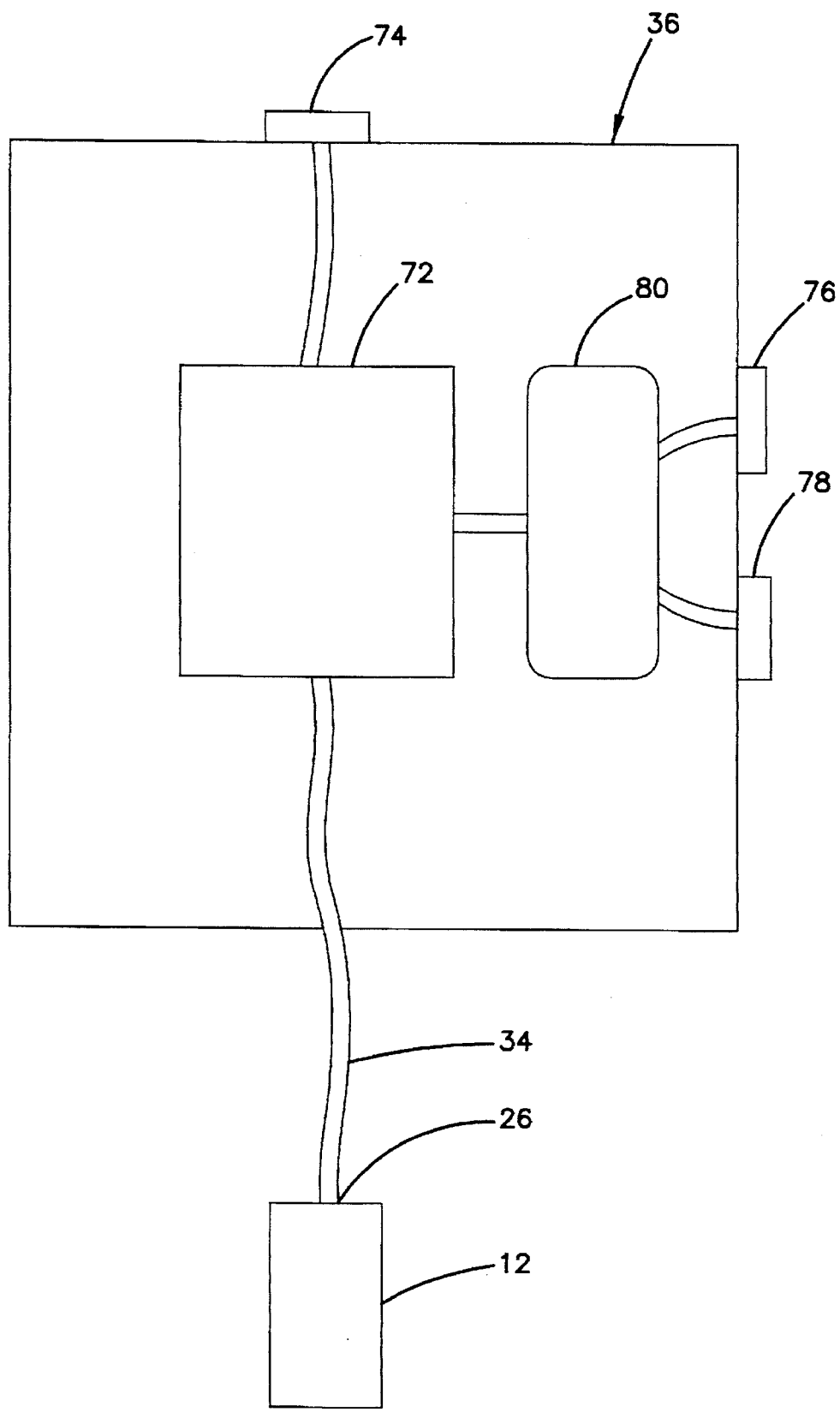
FIG. 3 is a schematic diagram of a modem useful in the communication systems shown in FIGS. 1 and 2 to interconnect a personal computer with a local pump or a remote pump.

Referring now to FIG. 3, device 36 is shown in greater detail. Device 36 includes the pump communications cable 34 which interconnects device 36 to pump 12 at communications port 26. Cable 34 extends from device controller 72 for selective connection to pump 12 at communications port 26. Device 36 further includes a computer communications port 74 for electrically linking modem 36 with computer system 30 through cable 38 as shown in FIG. 1 when pump 12 is to be locally downloaded with pump operation information, for example. Communication between local pump 12 and a local computer system 30 may be at 19,200 bps (bits per second) through controller 72 in a pass through configuration.

The operations system 10 of FIG. 1 is useful for downloading pump operation information from computer system 30 to pump 12. The information can be downloaded to one or more memory locations in pump 12 for storage. Once the information downloading operation is complete, pump 12 can be disconnected from device 36 and cable 34. This permits pump 12 to be conveniently carried about by the patient wherever the patient desires, such as around the home or around the patient's work place. Pump 12 is preferred to have a disabling function for disabling the fluid delivery system until device 36 and cable 34 are disconnected from pump 12. However, such operation of the pump is preferred but not mandatory.

Figure 2:
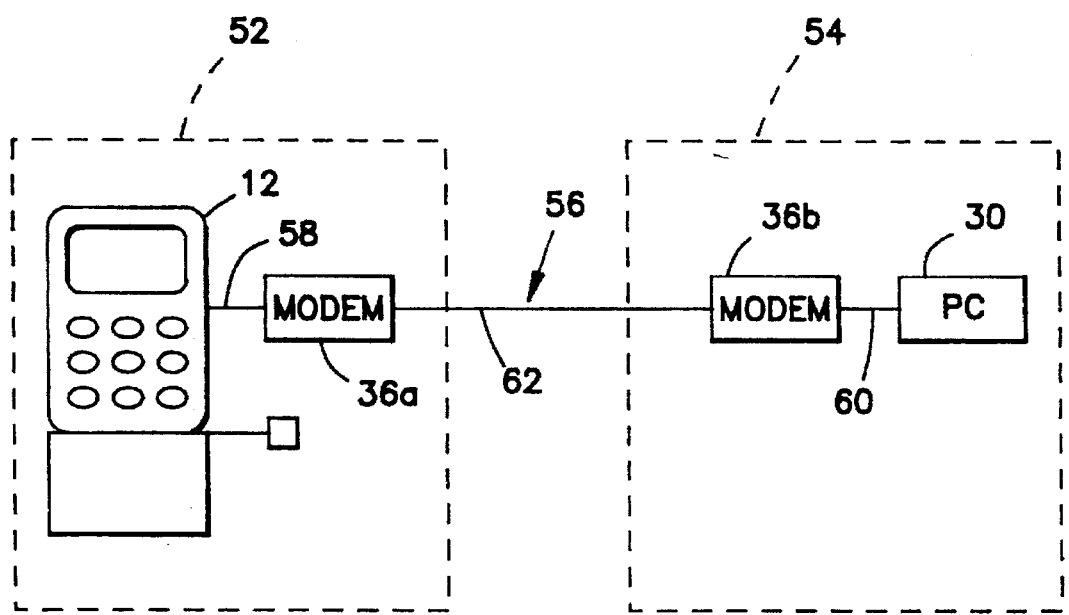
FIG. 2 is a schematic diagram illustrating the pump of FIG. 1 linked to a personal computer located at a remote site.

Referring now to FIG. 2, a second system 50 for operation of pump 12 is shown. In FIG. 2, pump 12 is located at a first site 52. Computer system 30 in FIG. 2 is located at a second site 54 which is remote from site 52. Remote communication means 56 permits communication between the pump 12 and computer system 30. Remote communication means 56 includes a first cable 58 or other communication structure linking pump 12 with a first modem 36a. A second cable 60 or other communications structure links computer system 30 to a second modem 36b. First cable 58 and second cable 60 may be RS232 serial communication cables. First and second modems 36a,36b may be identical to device 36. However, modems 36a,36b are not operated in the pass through configuration as is device 36 in system 10 of FIG. 1. First and second modems 36a,36b permit communication between remote sites over a communications medium 62 such as conventional telephone lines, cellular phone systems, fiber optics links, satellite links, microwave links, or other remote links. First and second modems 36a,36b may communicate at 9600 bps over conventional phone lines and include error correction and data compression features.

The second operations system 50 in FIG. 2 is useful to download pump operation information to pump 12 located at site 52 from a remote site 54. Remote downloading of pump operation information is useful since pump 12 does not have to be handled by the party who is downloading the pump operation information to pump 12 from the remote site. Site 52 may be the patient's home or work place and site 54 may be the caregiver's office or home. Alternatively, site 52 may be the caregiver's office, and site 54 may be the pump maintenance site or the pump manufacturing site.

As shown in FIG. 3, device 36 further includes a remote communications port 76 for linking device 36 to remote sites over communications medium 62. Communications port 76 permits communications between pump 12 and computer system 30 through modem 36b over communications medium 62 with modem 36a located locally with respect to pump 12 as is shown in FIG. 2.

As shown in FIG. 3, device 36 further includes a local phone communications port 78 to permit interconnection of a local phone (not shown) with device 36. Local phone port 78 permits use of the local phone such that the caregiver or other party can communicate by conventional telephone voice communication with the patient or other party located locally with respect to pump 12, before a modem link is established and after the modem link is terminated.

Device 36 of FIG. 3 permits information to be transmitted to and from computer system 30 located either locally with pump 12 or remotely to pump 12. If one mode of communications is not desired, then it is not necessary for device 36 to include apparatus for permitting both local and remote communications capability. For example, modems 36a,36b may not need local communications capability in the pass through configuration if the modems will not be used to link a local computer system with a local pump. Also, for the system of FIG. 1, if the only communication anticipated with pump 12 is local, then device 36 need only be constructed with the local communications apparatus to permit the pass through communications with electrical protection of the pump. Finally, if electrical protection is not needed, then only an electrical connection between pump 12 and computer system 30 needs to be provided in general and a direct cable download can be utilized.

Figure 4A:
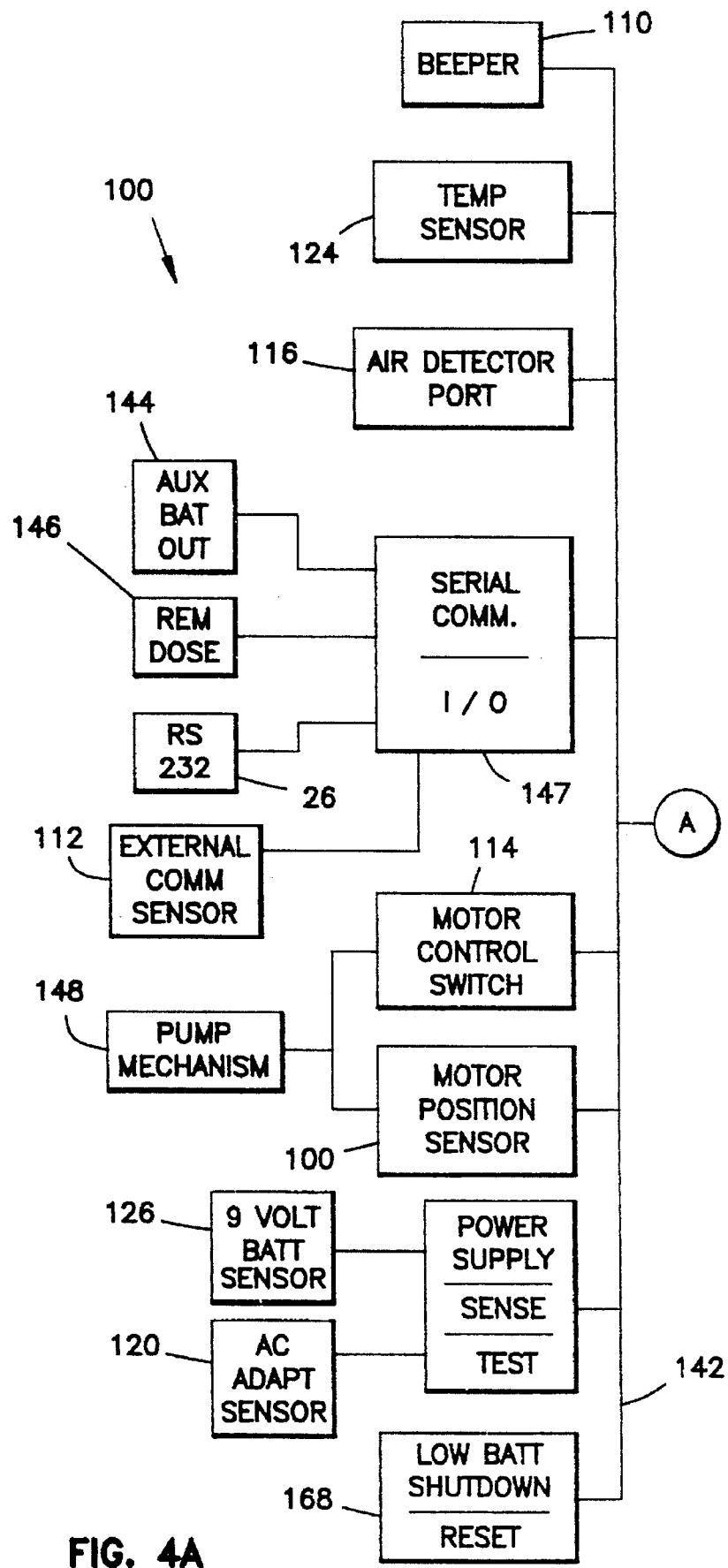
FIGS. 4A and 4B together show a block diagram of a control system for the pump shown in FIGS. 1 and 2.
Figure 4B:
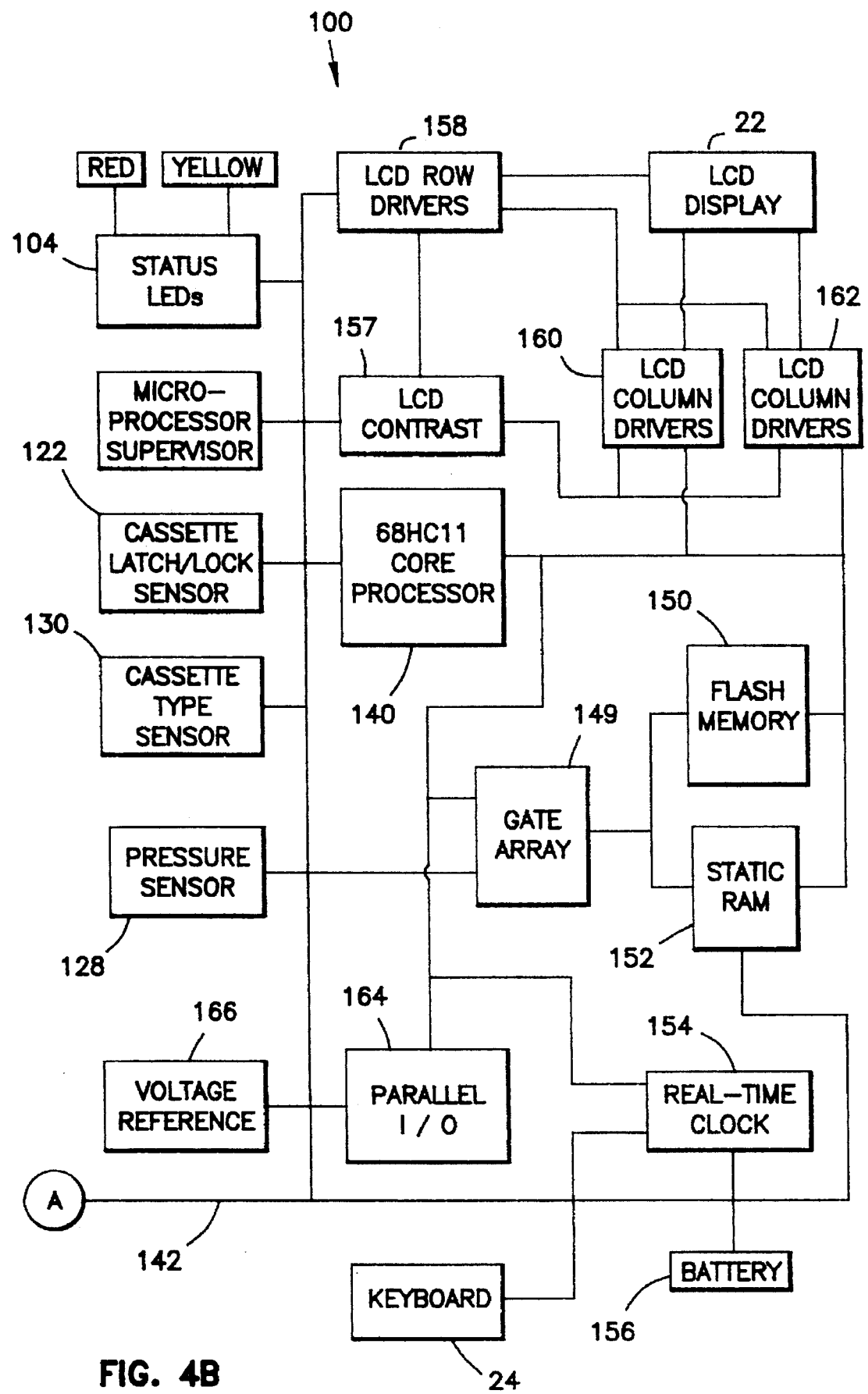

Referring now to FIGS. 4A and 4B, a block diagram is shown for a control system 100 of control module 14 of pump 12. Control system 100 controls operation of all the major functions of pump 12. Control system 100 of FIG. 4 includes display 22. Display 22 may be an LCD-type display for displaying information to the patient or caregiver.

Status LEDs 104, such as a red LED and a yellow LED, may be provided as part of control system 100 to provide an easily identifiable visual signal to the patient or caregiver regarding operations of the pump. The status LEDs may be operated to indicate any of a variety of conditions concerning pump 12. It is to be appreciated that other suitable status indicators might be used.

Control system 100 preferably includes keyboard 24 with a plurality of keys. In one preferred embodiment, nine different keys are provided. However, it is to be appreciated any number of keys could be provided with respect to pump 12. Keyboard 24 provides an input structure for the patient or the caregiver to enter information into control system 100 or to activate features of pump 12.

Control system 100 includes various sensors, switches, or devices needed or useful in operating the various features of pump 12. A motor position sensor 108 is provided for monitoring the position of the motor of the pumping mechanism. An appropriate signal is generated by sensor 108 and communicated to processor 140.

Beeper 110 provides an audible signal at the desired time to the user of pump 12. An appropriate signal from processor 140 activates beeper 110 at the appropriate time.

External communication sensor 112 senses when a communications cable connection is made with respect to pump 12 at communications port 26. An appropriate signal is generated by external communication sensor 112 and sent to processor 140 indicative of the connection and/or the lack of connection with the communications cable.

Motor control switch 114 turns on and off the motor of the pumping mechanism at the desired time based upon signals sent from processor 140. Pump 12 can be intermittently operated a predetermined number of times at predetermined intervals according to the pump operations program provided to the pump control system 100. These intervals can range from once every couple of seconds or less to as long as a couple of times an hour or more.

Air detector port 116 allows the plug in of an appropriate sensor to sense air in the fluid conduit between the reservoir and the patient.

AC adapter sensor 120 senses when an AC adapter has been plugged into pump 12 such that the pump is then powered by the alternating current power supply.

Cassette latch/lock sensor 122 senses when cassette 16 has been appropriately latched (mounted to control module) and also locked against unlatching from control module 14.

Temperature sensor 124 senses the ambient air temperature to provide an input to the pump operating program to increase the accuracy of the patient dosage. Tube compression properties can be affected by the ambient air temperature.

Battery sensor 126 senses the presence of a battery supply, such as a nine volt battery. Battery sensor 126 also senses when the battery supply is low.

Pressure sensor 128 senses high pressure in the conduit between the reservoir and the patient to detect when occlusions have occurred.

Cassette type sensor 130 senses indicia on cassette 16 for use in operating pump 12.

Auxiliary battery output port 144 is provided for supplying a source of power to an external accessory of pump 12 from the power supply of pump 12.

Remote dose cord port 146 permits interconnection of a remote dose cord arrangement to pump 12. The remote dose cord arrangement permits the patient to remotely press a key on keyboard 24, such as the key which manually operates the pumping mechanism, via a signal from a remote switch sent through remote dose cord port 146 to processor 140. A signal generated by an appropriate sensor at port 146 is sent to processor 140 to indicate to processor 140 that the remote dose cord has been properly connected to pump 12 or remains properly connected and/or that the remote dose cord has been activated.

A serial communication means 147 is provided for controlling communications access with auxiliary battery output port 144, remote dose cord port 146, and communications port 26 with sensor 112 in a serial manner.

Pumping mechanism 148 is illustrated as being controlled by motor control switch 114 and monitored by motor position sensor 108. Pumping mechanism 148 is responsible for pumping fluid from the reservoir to the patient. As noted above, one possible pumping mechanism includes a rotatable cam shaft with tube engaging followers reciprocally mounted to move as the cam shaft rotates.

The various sensors, switches, and devices in control system 100 generate and/or receive an appropriate signal or signals during communication with processor 140 during operation of pump 12. Processor 140 is electrically interconnected through an appropriate interface bus 142 with all of the various sensors, switches, and other devices of pump 12. The processor 140 responds to input signals by generating appropriate control output signals in accordance with the program control logic stored in memory. One preferred processor 140 that may be used in connection with pump 12 is an MC68HC11E9 high-density complimentary metal-oxide semiconductor (HCMOS) high performance microcontroller unit (MCU) by Motorola. Such processor includes 512 bytes of electrically erasable programmable read only memory (EPROM), and 512 bytes of random access memory (RAM).

Core processor 140 is further electrically interconnected to flash memory 150 and a static random access memory (RAM) 152. A real time clock 154 is also provided. Battery 156, such as a lithium cell, provides a power supply to the real time clock 154 and the static RAM 152. LCD contrast device 157, LCD row drivers device 158, and LCD column drivers devices 160,162 comprise at least a part of the control circuitry of display 22.

The flash memory 150 is utilized to store pump operation information which is accessed by the processor 140 for operating pumping mechanism 148 and the other sensors, switches, and devices of pump 12. Flash memory 150 permits pump operation information to be initially electrically written to flash memory 150 and subsequently stored in flash memory 150. Storage of the pump operation information in flash memory 150 is nonvolatile in that is does not require a continuous power supply to flash memory 150 to maintain the information stored in the memory. At a later time, flash memory 150 can be electrically erased, and rewritten with different pump operation information.

In one preferred embodiment, the program needed to run pump 12 is stored in the flash memory 150. Patient specific settings for pump 12 can be input via keyboard 24 or communications port 26 and stored in flash memory 150 or memory associated with processor 140. Examples of patient specific settings include rate of infusion, length of infusion, bolus information, security codes, and patient weight and sex. It is preferred to store such patient specific pump operation information in the memory of processor 140 or other memory location other than flash memory 150 due to limitations of flash memory 150 with respect to the number of times the memory can be erased and rewritten. Since the patient specific information is typically frequently changed in many of the anticipated uses of pump 12, it is not desireable to store this type of information in flash memory 150.

Static RAM 152 can be utilized to store some information relating to operation of the pump. Typically, intermediate information concerning pump operations is stored in the static RAM. Intermediate information may include calculation results from the pump operations program performed by processor 140. Pump usage information regarding pump operation events may be stored in static RAM 152, such as the number of start and stop events, the number of cassettes attached, and the total dosage pumped. An additional location for storage of pump operation information is the memory associated with the real time clock 154.

Flash memory 150 preferably includes a boot program which is preferably non-erasable. The boot program permits initialization and loading of pump operation information to the pump 12 via communications port 26. Further, a gate array 149 and/or flash memory 150 includes appropriate programming to handle incoming data from communications port 26 or keyboard 24 wherein the information is directed to the proper storage location if the information is not to be stored in flash memory 150. For example, remote programming may be utilized to enter the patient specific information into control system 100. The patient specific information may be entered initially or when changes occur over time due to changes in the specific therapy needed. For example, if the patient's condition improves or worsens, changes may need to be made in the specific patient settings. The flash memory 150 may include the appropriate program or programs to direct storage of the patient specific settings to the appropriate memory device in control system 100.

Flash memory 150 is an embedded memory associated with control module 14. Once installed in control module 14, flash memory 150 is not removed from pump 12. Flash memory 150 is electrically erasable and reprogrammable and does not require power to maintain the contents of its memory. A variety of flash memories may be used for flash memory 150. An example of one preferred flash memory which is usable in pump 12 is by Intel Corporation, and identified as 28F008SA 8 MBIT (1 MBIT×8) Flashfile™ memory. Such memory is useful in pump 12 for handling pump operations information associated with the various features provided on pump 12. The Intel product is useful in that it includes separately erasable and reprogrammable blocks of memory, at least one of which can be blocked from erasure once programmed with the desired information.

Processor 140, flash memory 150, static RAM 152, gate array 149, real-time clock 154, and parallel input/output means 164 comprise at least a part of the processor control circuitry of control system 100.

As shown in FIG. 4B, a voltage reference 166 is provided as part of control system 100 in the preferred embodiment. As shown in FIG. 4A, a low battery shutdown and reset device 168 is provided in control system 100 in the preferred embodiment.

Pump 12 may be utilized for a variety of different therapy types or applications. For example, pump 12 may be used as a pump in: 1) a pain control therapy, or patient controlled analgesia; 2) a nutrition therapy, or total parenteral nutrition therapy; 3) a chemotherapy program or therapy; or 4) an antibiotic therapy. Other applications are possible. The different applications may involve different operations of pumping mechanism 148 and the other switches, sensors, and other devices in pump 12. For example, the volume of fluid per unit time pumped by the pumping mechanism 148 may be continuous or it may be changed over time. A bolus amount (increased dosage) pumped by the pumping mechanism 148 may be provided once or at periodic intervals. The bolus amounts and/or the bolus intervals may be varied over time. The patient may be given limited ability to increase the dosage when the patient desires by causing extra activations of the pumping mechanism 148 through a dose key.

As another example, there may be lock out access to the patient wherein various keys of keyboard 24 are inoperative such that the patient cannot change the therapy prescribed by the caregiver unless the caregiver removes the lock out feature. Each application may have different lock out features.

Calculations by the processor may be needed to achieve a certain total dosage over a certain time even though the patient may be able to increase the dosages at one or more times during the therapy. Inputs to pump 12 may include reservoir size, activation amount, and/or drug concentration. In some cases, it is desireable for pump 12 to calculate the desired number of activations and intervals to achieve a certain drug level in a patient having a certain sex and weight. Each application may involve different calculations performed by pump 12.

Other sensors, switches, and devices of pump 12 may be operated differently in different therapies. The pump control program stored in the memory of pump 12 including flash memory 150 includes information relating to the various aspects of pump 12 needed to deliver the appropriate therapy. In one preferred pump 12, flash memory 150 contains the general application or operating program (such as pain, nutrition, antibiotic, or chemotherapy) which is accessed by processor 140 during usage of pump 12. It is preferred that only one application be stored in flash memory 150 as a safety precaution against the caregiver or the patient inadvertently running the wrong program.

The patient specific information needed to operate pump 12 for the specific application is stored in the memory associated with processor 140 and is utilized by the processor 140 when needed with respect to the pump applications program. Any intermediate calculation information or other pump information, including specific pump usage information, may be stored in any of the various memories. Static RAM 152 provides a useful memory location for storage of the intermediate information.

Pump 12 can be programmed from computer system 30 in a variety of different ways. In one method, computer system 30 can include a single pump application program stored in its memory. The caregiver or pump supplier would download the pump application program from computer system 30 to flash memory 150 of pump 12. Alternatively, computer system 30 can include a plurality of different pump application programs. The caregiver or pump supplier can select the desired program to be downloaded to flash memory 150 of pump 12. Alternatively, computer system 30 can include one or more pump application programs that each include options for selection by the caregiver or pump supplier for each pump application program. Once the options are selected, the caregiver can download the pump application program generated by the caregiver to flash memory 150 of pump 12. In the above methods, it is anticipated that the caregiver would not generate the code for the pump application program. The code would be supplied by the pump supplier or other programming specialist. This is a safety feature as well as convenience to the caregiver. The caregiver need only be familiar enough with computer system 30 to set up the link to pump 12 and then select and download the appropriate pump application program. It is to be appreciated that, in some cases, the caregiver will have sufficient expertise to generate the code for the pump application program. Similar safety and convenience features are present with respect to any programming of the patient specific parameters downloaded from computer system 30. User prompts are preferably provided for requesting the caregiver to enter the particular settings when entered via computer system 30.

Flash memory 150 is used to advantage in pump 12. Unlike removable memory devices, there is no large opening in the pump housing associated with the memory which needs to be protected from tampering, contaminants or moisture. No fragile parts are accessible via communications port 26 from a mechanical protrusion as they would in the case of card readers having relatively large openings to receive the card. The communications port 26 is relatively easy to protect from contaminants and moisture. There is also no loose cartridge or card that could be dislodged, tampered with, damaged or lost. The patient or the caregiver does not need to be concerned that the removable memory device, such as the card or cartridge, is properly positioned in the opening in the pump as in the case of pumps utilizing the separate memory cards or cartridges. This is especially important when the patient is using the pump in an unsupervised location. Should a card or cartridge become dislodged from the pump, there is a concern that the pump would cease operation and the patient would be unable to restart the pump. The use of flash memory 150 eliminates these problems.

Another advantage of flash memory 150 is that neither the caregiver nor the patient needs to maintain any separate memory cartridges or cards for different therapies. There is no need for the caregiver to keep track of any cards, cartridges or other pieces separate from the pump. Disposal or destruction of outdated cards is no longer a problem. Since no card or cartridge reader needs to be provided, there is a reduction in the size of pump 12.

Another advantage of providing flash memory 150 is that there is no need to open up the housing and remove a chip or other wired-in-memory device in order to reprogram the pump. Changes to the applications stored on flash memory 150 are done electronically via the input/output communications port 26. Virtually any programmed function of pump 12 can he electrically changed if desired. As yet undeveloped improvements can he added as they are completed. Caregivers do not need to worry about their pumps becoming obsolete as long as new operating programs are developed. There are no mechanical changes needed for the memory connections to the rest of the pump control system when the flash memory is reprogrammed. Handling of the new chips prior to and during installation is no longer a concern. Disposal or destruction of the old chips is no longer a problem. Applications updates needed by the caregiver can be handled via a floppy disk mailed to the caregiver whereby the caregiver can download the updated program to the pump or the inventory of pumps maintained by the caregiver. Alternatively, the applications updates can be transmitted over the telephone lines via modems to the caregiver.

No special expertise is needed to reprogram as is the case of pumps where chips must be removed and replaced to change the memory.

Pump 12 provides system of pumping fluid to a patient where pump 12 is very flexible in how the control system 100 operates. Unlike pumps using EPROM memory for storing the pump operating program, pump 12 with control system 100 is easily changeable as needs and circumstances change. No chips need to be removed or specially handled to reprogram. At the same time, pump 12 is tamper resistent, contamination resistent, and reliable during operation, unlike pumps with replaceable cards.

A further advantage of flash memory 150 is the ability to remotely program flash memory 150. Such remote programming is not possible with cards or cartridges which need to be changed, or replaceable EPROMs which need to be physically handled and reprogrammed. Remote programming can be done initially prior to the first use of the pump or at a later date after initial operation of the pump. The applications can be easily reprogrammed if a bug is identified or if improvements are made in the application program. Applications updates needed by the caregiver can be handled via the telephone lines. Also, changes can be made to the operating program midway through the therapy to address changes in the patient's condition.

Another advantage of the present invention is that custom programs for caregivers who desire particular operating programs for their inventory of pumps are possible through the use of flash memory 150. Individual patients may require a custom program. Flash memory 150 permits the custom program to be quickly downloaded to the patient either locally or remotely via communications port 26. Once the patient no longer needs the custom program, the pump is easily electrically reprogrammed via communications port 26.

Flash memory 150 has sufficiently large memory capability to store the operating program needed to run pump 12, including all of the sensors, switches, and devices.

Since a caregiver can reprogram the pump 12 when the pump is needed for a different application, less inventory of pumps is required by the caregiver. Flash memory 150 permits each pump to be utilized in more than one application over time depending on the immediate needs of the patients. Also, pump 12 may be simpler to operate if only one application is stored in the memory of pump 12. With only one application program stored in the memory, it is not possible for the wrong application program to be selected, once pump 12 is properly programmed. This is a safety feature for protecting the patient from inadvertently receiving the wrong therapy even though a correct drug cartridge is attached.

In some illnesses or treatments, a patient may desire successive different uses of pump 12. For example, some chemotherapy programs are preceded by a nutrition therapy to build up the patient's reserves of fluids or other nutrients. In that case, the memory of pump 12 does not need to simultaneously store both a nutrition therapy application and a chemotherapy application. In that case, the patient would utilize pump 12 with a nutrition therapy application programmed into flash memory 150. At the appropriate time, flash memory 150 could be reprogrammed with the chemotherapy application.

Keyboard 24 can intentionally be provided with a limited number of keys to keep operation of pump 12 through keyboard 24 simple. However, some applications and even some patient specific settings may involve numerous inputs such that the use of a standard keyboard, through computer system 30 may be advantageous. Downloading of this information from a computer system 30 is useful since all of the inputs of information can be made through a standard keyboard of computer system 30. The present invention provides the caregiver with the ability to download just applications to flash memory 150, or applications to flash memory 150 and patient specific settings to the other memory locations without entering information through keyboard 24.

Since reprogramming of flash memory 150 can only take place with a computer system 30, electronically monitoring the status of the pumps is easier. An updated status check, using appropriate status check program means stored in computer system 30 and/or in pump 12 (for example stored in flash memory 150), can be made of the pump each time there is an application download to the flash memory 150 or each time the pumps 12 are returned to the caregiver after use. The status program means for tracking pump status can help monitor the pumps which are configured for specific types of therapies. The status program means can also include patient name, address and telephone number, and pump location. There are advantages for caregivers and/or pump suppliers to have quick access to status reports on the configuration of the inventory of pumps maintained by the caregiver or supplier. The caregiver or supplier may need to quickly identify particular pumps in case a problem develops where the pumps must be recalled or reprogrammed. Use of computer system 30 to reprogram pump 12 provides a useful way to tie in status tracking software for automatic tracking of each pump 12. The status program means can include recertification tracking program means which automatically flags pumps needed for recertification of the operating systems.

The status program means can be general to only track pump configuration and/or time since recertification. The status program means can also download specific detailed pump operation information from pump 12 to computer system 30 pertaining to the therapy given. Examples of pump operation information that may be sent to computer system 30 from pump 12 include: drug type used, amount of drug used, type of pump operating program used, any changes to pump operating program, dates of pump usage, and a record of all pump start and stop events, number of cassettes used, occurrence of alarms, and other pump usage events. Such information is useful to the caregiver and to the pump supplier/manufacturer. Some of the relevant status information can be entered via the keyboard of computer system 30, instead of from pump 12, at the time of programming before the therapy or at the time of reprogramming after the therapy, such as date information.

Another advantage due to the presence of flash memory 150 having to be reprogrammed with a computer system 30 is that appropriate diagnostic program means for checking pump control system 100 and other features can be downloaded to flash memory 150 each time a programming operation occurs. The diagnostic program means need only be temporarily downloaded to flash memory 150. The diagnostic program means runs through various checks of control system 100 to verify that pump 12 and the associated switches, sensors, and devices are functioning properly. The diagnostic program means is then removed or erased from flash memory 150 and the new application program is downloaded onto flash memory 150. In this manner, any errors in pump 12 can be identified each time a pump 12 is programmed. Such diagnostic program can be downloaded to pump 12 initially before pump 12 is ever programmed to operate as a pump, or at a later date when pump 12 is reprogrammed.

The invention is not to be construed as to be limited by the specific embodiments described above or shown in the drawings, but is to be limited only by the broad general meaning of the following claims.

What is claimed is:

1. A pump system for infusing fluid into a patient, the pump system comprising:
   a pump for pumping fluid;
   a microprocessor configured to control the pump;
   a flash memory electronically connected to the microprocessor, the flash memory being partitioned into blocks of memory, the flash memory storing a boot program and a plurality of application programs, one of the application programs being a predetermined application program; and
   wherein the boot program is configured to launch the predetermined application program and the application programs are configured to control operation of the pump.

2. The pump system of claim 1 further comprising a communications port, the communications port being electrically connected to the microprocessor to permit the transfer of data into the pump system.

3. The pump system of claim 1 wherein each application program implements a fluid delivery algorithm, the fluid delivery algorithm controlling the amount of fluid that is delivered and the time the fluid is delivered.

4. The pump system of claim 1 further comprising an additional memory, the additional memory being electrically connected to the microprocessor.

5. The pump system of claim 4 wherein the additional memory is a random access memory.

6. The pump system of claim 5 wherein the additional memory is internal to the microprocessor.

7. The pump system of claim 4 wherein the additional memory includes patient specific information, the patient specific information including a rate of infusion, length of infusion, and bolus information.

8. The pump system of claim 7 wherein the specific information stored in the additional memory further includes security codes, patient weight, and patient gender.

9. The pump system of claim 1 further comprising:
   a communications port, the communications port being electrically connected to the microprocessor to permit the transfer of data into the pump system;
   an additional memory, the additional memory being electrically connected to the microprocessor; and
   data distribution circuitry, the data distribution circuitry being electrically connected to the microprocessor, to the flash memory, and to the additional memory, the data distribution circuitry configured to distribute data received at the communication port to the flash memory and the additional memory.

10. The pump system of claim 9 wherein the data distribution circuitry is formed from program code stored in the flash memory and executed by the microprocessor.

11. The pump system of claim 9 wherein the data distribution circuitry is formed from a gate array electrically connected to the flash memory and the additional memory.

12. A method of operating a pump system wherein the pump includes a microprocessor and a flash memory in electrical communication with the microprocessor, the flash memory storing a boot program and a plurality of application programs, one of the application programs being a predetermined application program, the method comprising the steps of:
   applying power to the microprocessor and the flash memory;
   executing the boot program;
   launching the predetermined execution program; and
   executing the predetermined application program, wherein the predetermined execution program controls operation of the pump.

13. The method of claim 12 wherein the pump system further includes an additional memory, the method comprising the additional steps of:
   inputting data into the pump system; and
   routing the information to the additional memory if the data includes patient specific settings.

14. A method of operating a pump system wherein the pump includes a microprocessor, a flash memory in electrical communication with the microprocessor, an additional memory in electrical communication with the microprocessor, the flash memory storing a boot program, the method comprising the steps of:
   applying power to the pump system; and
   executing the boot program, the boot program performing the steps of:
      determining whether a remote processor is interfaced to the communication port and configured to transmit data; and
      if a remote microprocessor is interfaced to the communication port, downloading the information; and
      storing the information.

15. The method of claim 14 comprising the additional step of routing information to the flash memory if the information is code for an application program, or to the additional memory if the information is patient specific settings.

16. The method of claim 15 wherein the pump system further includes data distribution circuitry and the data distribution circuitry performs the step of routing information.

17. A method of operating a pump system wherein the pump includes a microprocessor, a flash memory in electrical communication with the microprocessor, and a communication port in electrical communication with the microprocessor, the flash memory storing a boot program, the method comprising the steps of:
   applying power to the pump system; and
   executing the boot program, the boot program performing the steps of:
      determining whether a remote system is interfaced with the communication port and whether the remote system is configured to download code for an application program;
      downloading the code for the application program if remote system is interfaced with the communication port and the remote system is configured to download code for an application program; and
      storing the code for the application program in the flash memory.

18. The method of claim 17 wherein the flash memory is configured into blocks of memory addresses, the step of storing the code for the application program including the step of storing the code for the application program in a predetermined block of memory addresses.

* * * * *